United States Patent [19]

Spence

[11] 4,272,514

[45] Jun. 9, 1981

[54] HIGH ABSORPTION BODY POWDER

[75] Inventor: Wayman R. Spence, Waco, Tex.

[73] Assignee: Spenco Medical Corporation, Waco, Tex.

[21] Appl. No.: 91,391

[22] Filed: Nov. 6, 1979

[51] Int. Cl.$^3$ .......................... A61K 7/26; A61K 7/38
[52] U.S. Cl. ............................. 424/69; 260/17.4 ST
[58] Field of Search .................. 424/69; 260/17.4 ST

[56] References Cited

U.S. PATENT DOCUMENTS

| | | | |
|---|---|---|---|
| 2,614,945 | 10/1952 | Krisan | 424/69 |
| 3,278,383 | 10/1966 | White et al. | 424/69 |
| 3,579,628 | 5/1971 | Gander et al. | 424/28 |
| 3,669,103 | 6/1972 | Harper et al. | 128/156 |
| 3,954,721 | 5/1976 | Gross | 526/14 |
| 3,966,679 | 6/1976 | Gross | 260/47 EA |
| 3,980,663 | 9/1976 | Gross | 260/29.6 TA |
| 3,985,616 | 10/1976 | Weaver et al. | 195/63 |
| 3,997,484 | 12/1976 | Weaver et al. | 260/17.4 ST |
| 4,008,353 | 2/1977 | Gross et al. | 428/522 |
| 4,017,653 | 4/1977 | Gross et al. | 427/385 A |
| 4,018,951 | 4/1977 | Gross | 427/401 |
| 4,055,184 | 10/1977 | Karami | 128/287 |
| 4,058,124 | 11/1977 | Yen et al. | 128/284 |
| 4,123,397 | 10/1978 | Jones | 260/17.4 GC |
| 4,155,893 | 5/1979 | Fujimoto et al. | 260/29.6 H |
| 4,159,260 | 6/1979 | Jones et al. | 260/17.4 ST |

OTHER PUBLICATIONS

Weaver et al., A Practical Process for the Preparation of Super Slurper, A Starch Based Polymer With a Large Capacity To Absorb Water, U.S.D.A. pub. Mar. 23, 1977.

Ed Silk, NonWovens Industry, pp. 19-20, "Superabsorbents Update-More Firms Showing Interest in 'Supers' As New Products are Introduced," Nov. 1977.

Formed Fabrics Industry Publication, "Absorbent Starch-Based Co-polymers, Their Characteristics and Applications".

General Mills Chemicals, Inc. Brochure, "SGP Absorbent Polymer".

Primary Examiner—Alan L. Rotman
Attorney, Agent, or Firm—Richards, Harris & Medlock

[57] ABSTRACT

High absorption body powder compositions are provided that contain a mixture of a water absorbent graft copolymer and an organic or inorganic adjuvant sorbent such as talc.

13 Claims, No Drawings

HIGH ABSORPTION BODY POWDER

BACKGROUND OF THE INVENTION

The pharmaceutical and cosmetic industries have long provided to the consuming public body powders used primarily for abosrbing moisture that may be secreted from the sebaceous and sweat glands, for example. Body powders are often used on babies to help prevent diaper rash and to otherwise help maintain dryness.

Since one of the primary purposes of body powders is to absorb moisture, the effectiveness of the body powder is lost when the powder has reached its capacity for absorbence. Generally, talc is the primary abosrbent constituent in body powders. Since talc, other inorganic sorbents, and organic sorbents, such as starch and cellulose generally have a relatively low capability of water absorption, a need exists for a body powder having improved characteristics, namely, improved absorbency. Further, since high absorption polymers tend to form a tenacious mass or gel upon absorption of a fluid, a need exists for a body powder having high sorbency relative to inorganic sorbents without forming a tenacious mass or gel after sorption of such fluid.

SUMMARY OF THE INVENTION

The present invention provides an improved body powder that is capable of absorbing relatively large quantities of water and other fluids secreted by the body, such as from the sebaceous and sweat glands, for example.

The improved body powder of the present invention comprises a mixture of a first component, a powdered water absorbent polymer, and a second component, an inorganic or organic adjuvant sorbent. The preferred polymer is a hydrolyzed starch-polyacrylonitrile graft copolymer and the preferred inorganic sorbent is talc. The body powder may also include optional components such as germicidal compounds, antiseptics and perfumes. Preferably, the graft copolymer is present in the mixture in an amount of from about 2% to 50% by weight and most preferably about 20% by weight of the total composition.

The mixture of the polymer and inorganic sorbent results in a composition that absorbs fluid and resists formation of a tenacious mass or gel after absorbing fluid, such as, for example, after being applied to a person's skin.

DETAILED DESCRIPTION OF THE INVENTION

According to the invention, a body powder composition is provided that has a substantially greater capacity to absorb water, sebaceous and sweat gland excretions from the human body and other fluids compared with conventional body powders that contain primarily talc for absorbency.

According to the invention, the improved high absorption body powder composition comprises a mixture of a first component, a powdered water absorbent graft copolymer, and a second component, an organic or inorganic sorbent. As used herein, the term "mixture" means a heterogeneous association of substances. Preferably, the substances contained in the body powder composition of the present invention are uniformly dispersed. Both components should be non-toxic and otherwise produce no harmful physiological results when applied to a person's skin.

The preferred type of water absorbent graft copolymer present in the improved body powder of the present invention is a hydrolyzed starch-polyacrylonitrile graft copolymer. Hydrolyzed starch-polyacrylonitrile graft copolymers exhibiting the capacity to absorb relatively large quantities of water, from about 100 to about 2000 times their weight of deionized water are known at this time. The hydrolyzed starch-polyacrylonitrile graft copolymers may be produced by exposure of a mixture of acrylonitrile and starch, either gelatinized or ungelatinized, to a cerium salt, such as cerium ammonium nitrate, which acts as a catalyst to generate free radicals. Other systems (such as ferrous sulfate-hydrogen peroxide or $\gamma$-radiation) capable of producing starch-acrylonitrile graft copolymers may be used. Polyacrylonitrile chains form at the site of these free radicals. The resulting material is then saponified in alkali such as sodium hydroxide to hydrolyze the polyacrylonitrile chains to carboxamide and alkali metal carboxylate groups mixed with metal salts. After drying, the material can absorb about 100 to about 400 times its weight of deionized water. Drying can be accomplished by drum, tumble, air, vacuum drying or any other suitable method known to those skilled in the art. Isolation of the copolymer by precipitation with alcohol before drying provides a material capable of absorbing from about 800 to about 1500 times its weight of deionized water. The fluid absorbency of the copolymer is determined by suspending a weighed amount of dry copolymer in an excess of deionized water and filtering the resulting solution to recover the unabsorbed fluid.

Prior to the utilization of the copolymer according to the invention, the unreacted monomeric acrylonitrile is separated from the graft copolymer. Preferably, this is done prior to saponification. This can be accomplished by any method known to those skilled in the art, such as by steam distillation. The graft copolymer used in accordance with the invention must be nontoxic and physiologically acceptable. The water insoluble form of the hydrolyzed starch-polyacrylonitrile graft copolymer is used in accordance with the invention. Preferred hydrolyzed starch-polyacrylonitrile graft copolymers for use in accordance with the invention and methods of manufacture are disclosed in U.S. Pat. No. 3,935,099 to Weaver et al. which is herein incorporated by reference. Such graft copolymers generally have molecular weights of about 50,000 to about 500,000. Unmodified corn starch is the preferred type of starch for use in synthesizing graph copolymers for use in accordance with the invention, primarily because of low cost and availability.

While either organic or inorganic sorbents or mixtures thereof can be used as adjuvant sorbents in the compositions of the present invention, inorganic sorbents are preferred. As used herein, "adjuvant sorbent" is used interchangeably with the organic or inorganic sorbent. Further, "adjuvant sorbent" does not include those polymers as described aforesaid and includes only those sorbents which exhibit relatively low sorbent capacities, generally on the same order of magnitude as the sorbent capacity of talc. The water sorption capacity of the adjuvant sorbent is much less than those of the graft copolymer and, in effect also acts as a diluent for the graft copolymers. However, the presence of the adjuvant sorbent assures that the subject composition flows, spreads and adheres to the body in a conventional manner and generally efficiently functions as a body powder.

For example, the inorganic adjuvant sorbents which can be used within the scope of the invention include silicates of aluminum, calcium and magnesium. Some specific examples of commonly occurring materials which can be used within the scope of the invention include: Kaolinite, $Al_2(SiO_5)(OH_4)$; Dickite, $Al_2(Si_2O_5)(OH)_4$; Nacrite, $Al_2(Si_2O_5)(OH)_4$; Metahalloysite, $Al_2(Si_2O_5)(OH)_4$; Pyrophyllite, $Al_2(Si_4O_{10})(OH)_2$; Talc, $Mg_3(Si_4O_{10})(OH)_2$; and Montmorillonite, $Al_2(Si_4O_{10})(OH)_2 \cdot xH_2O$, $Mg(Si_4O_{10})(OH)_2 \cdot xH_2O$.

The preferred type of inorganic adjuvant sorbent according to the invention is talc. Talc is a natural hydrous magnesium silicate.

Organic adjuvant sorbents may be used in the compositions of the present invention. Suitable organic sorbents include materials such as powdered starches and celluloses and any other organic sorbents which have been heretofore used as body powders. In other words, the inorganic or organic adjuvant sorbent must be useful as a body powder and will generally have a water sorption capacity on the same order of magnitude as talc.

According to the invention, the water absorbent graft copolymer is present in an amount of from about 2% to about 50% by weight and preferably about 20% by weight of the total body powder composition. The organic or inorganic sorbent is present in an amount of from about 50% to about 98% by weight of the total body powder composition. A preferred weight ratio of polymer to sorbent is about 1:4, respectively.

In order for effective use as body powder, the polymer should have a particle size of less than about 150 mesh (U.S. Std.) and preferably from about 200 to about 400 mesh (U.S. Std.) Generally, the particle size of the polymer used will not be smaller than about 5 microns. The preferred particle size of the adjuvant sorbent included in the body powder according to the invention is between about 5 microns and about 25 microns, although the particle size of the adjuvant sorbents may be as high as about 100 microns. The desired particle sizes can be attained by grinding. Grinding can be accomplished through the use of a hammer mill, jet mill, fluid-energy mill or any other device or method known to those skilled in the art. When referring to particle size of the components of the body powder, it is to be understood that at least about 95% by weight of the component should have a particle size in that particular range or about that particular size.

The improved high absorption body powder of the present invention is prepared by mixing the desired quantities of comminuted water absorbent graft copolymer and the adjuvant sorbent until a uniform heterogeneous mixture is formed. The components making up the body powder may be ground to the desired particle size range either before or after the components are mixed together.

The body powder of the present invention results in a high absorption body powder that, when applied to a person's body, for example, will be highly absorbent but will not result in a tenacious or sticky mass or gel after fluid absorption. Thus, the combination of adjuvant sorbent and high absorption polymer results in an improved body powder that is highly absorbent. The relatively small particle size of the sorbent causes it to act as a lubricant for the copolymer and prevents the copolymer from forming a tenacious mass or gel after absorbing a fluid.

The high absorption body powders of the present invention may also optionally contain germicidal compounds or antiseptics, including such materials as quaternary ammonium salts and the phenols, oxyquinoline sulfate and many other germicidal and antiseptic compounds that normally may be included in body powders. In addition, boric acid may be present in the body powders of the present invention to provide a slight antiseptic property. The body powder according to the present invention may also be slightly perfumed, usually with not more than 0.25% of perfume by weight of the total composition.

While the invention has been described with respect to preferred embodiments, it is to be understood that numerous changes, modifications and substitutions may be made and are intended to be covered by the appended claims.

I claim:

1. An improved high absorption body powder composition comprising a uniform mixture of a water-absorbent graft copolymer and an adjuvant sorbent, said copolymer having a particle size of less than about 150 mesh and characterized by a relatively high water absorption capacity, said adjuvant sorbent having a particle size of about 100 microns and less, and characterized by a low water sorbent capacity relative to said water absorbent graft copolymer, said body powder containing said polymer in an amount of from about 2% to about 50% by weight of said composition and said adjuvant sorbent in an amount of from about 50% to about 98% by weight of said composition.

2. The body powder composition as recited in claim 1 wherein said copolymer is a hydrolyzed starch-polyacrylonitrile graft copolymer.

3. The body powder composition as recited in claim 2 wherein said copolymer has a molecular weight of from about 50,000 to about 500,000.

4. The body powder composition as recited in claim 2 or 3 wherein said graft copolymer is synthesized from unmodified corn starch.

5. The body powder composition as recited in claim 1 wherein said adjuvant sorbent is selected from the group consisting of magnesium silicates, aluminum silicates, calcium silicates, starch, and cellulose powder.

6. The body powder composition as recited in claim 1, 2 or 5 wherein said copolymer has a particle size of from about 200 to 400 mesh and said sorbent has a particle size of from about 5 microns to about 25 microns.

7. The body powder composition as recited in claim 1, 2 or 5 wherein said polymer is present in an amount of about 20% by weight of said composition and said sorbent is present in an amount of about 80% by weight of said composition.

8. The body powder composition as recited in claim 1, 2 or 5 wherein said polymer and sorbent are present in a respective ratio of about 1:4.

9. An improved high absorption body powder composition comprising a mixture of a hydrolyzed starch-polyacrylonitrile graft copolymer having a molecular weight of from about 50,000 to about 500,000 and talc.

10. The body powder composition as recited in claim 9 wherein said talc is present in a particle size of from about 5 micron to about 25 micron and said copolymer is present in a particle size of about 200–400 mesh.

11. The body powder composition as recited in claim 9 or 10 wherein said copolymer and said talc are present in a respective ratio of about 1:4.

12. The body powder composition as recited in claim 9 or 10 wherein said copolymer is present in an amount of from about 2% to about 5% by weight of said total composition.

13. The body powder as recited in claim 9 or 10 wherein said copolymer is present in an amount of about 20% by weight of said total composition.

* * * * *

Notice of Adverse Decision in Interference

In Interference No. 101,494, involving Patent No. 4,272,514, W. R. Spence, HIGH ABSORPTION BODY POWDER, final judgment adverse to the patentee, was rendered Apr. 28, 1986, as to claims 1-3.

[*Official Gazette June 17, 1986.*]